Figure 4:
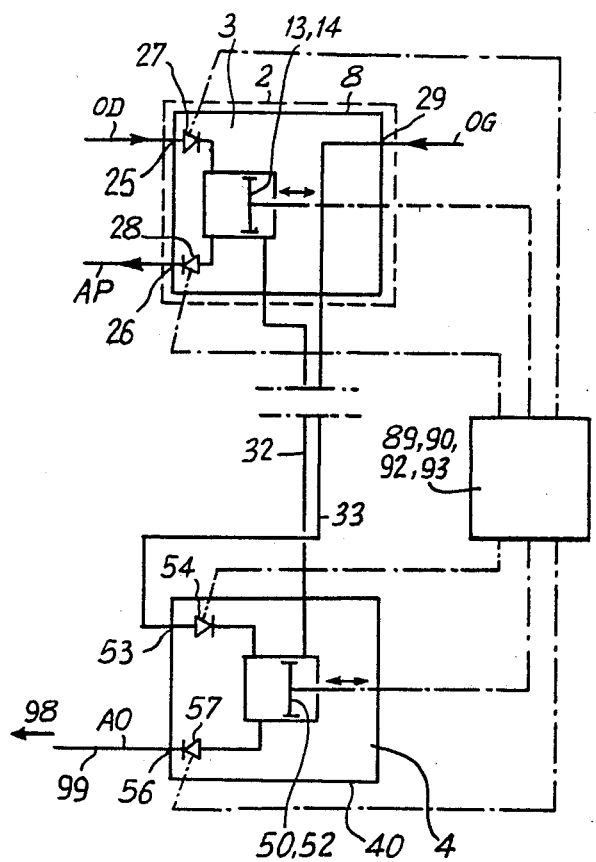

United States Patent [19]
Chareire et al.

[11] Patent Number: 4,820,301
[45] Date of Patent: * Apr. 11, 1989

[54] TOTAL ARTIFICIAL HEART COMPRISING TWO DISCONNECTED PUMPS ASSOCIATED INTO ONE FUNCTIONALLY INDISSOCIABLE UNIT

[75] Inventors: Jean-Louis Chareire, Levallois; Didier Lapeyre, Pacy-Sur-Eure, both of France

[73] Assignee: Aerospatiale Societe Nationale Industrielle, Paris, France

[*] Notice: The portion of the term of this patent subsequent to Nov. 18, 2003 has been disclaimed.

[21] Appl. No.: 941,044

[22] Filed: Dec. 12, 1986

[30] Foreign Application Priority Data

Dec. 12, 1985 [FR] France ................. 85 18425

[51] Int. Cl.$^4$ .............................................. A61F 2/22
[52] U.S. Cl. .................................................. 623/3
[58] Field of Search ........................................ 623/3

[56] References Cited

U.S. PATENT DOCUMENTS

| | | | |
|---|---|---|---|
| 4,105,016 | 8/1978 | Donovan | 623/3 |
| 4,195,623 | 4/1980 | Zeff | 623/3 |
| 4,623,350 | 11/1986 | Lepeyre et al. | 623/3 |

FOREIGN PATENT DOCUMENTS 8318368 2/1983 Japan .

*Primary Examiner*—Richard J. Apley
*Assistant Examiner*—James Prizant
*Attorney, Agent, or Firm*—Fisher, Christen & Sabol

[57] ABSTRACT

This invention relates to a total artificial heart intended to replace a diseased human heart. According to the invention, this prosthesis comprises a pericardial module and an abdominal module, incorporating their own electro-mechanical pumping system and connected to each other by a blood and gaseous link. The pericardial module acts as right-hand part of the heart and the abdominal module as left-hand part of the heart. This abdominal module is connected to the abdominal aorta by a connection.

9 Claims, 2 Drawing Sheets

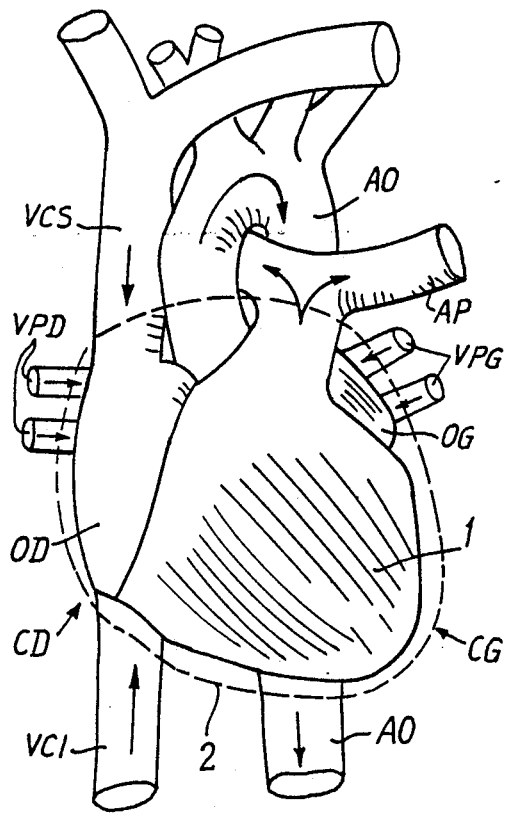
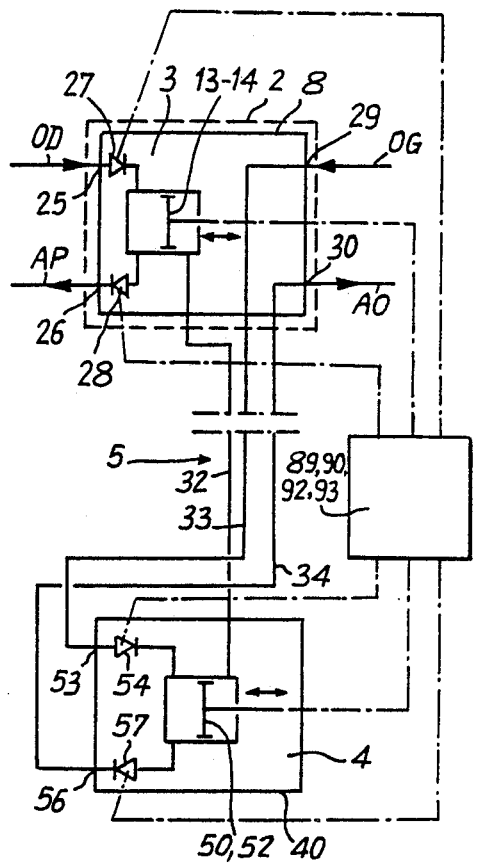
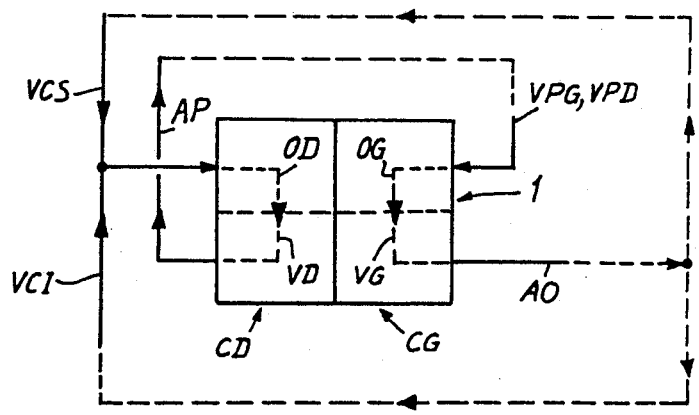

TOTAL ARTIFICIAL HEART COMPRISING TWO DISCONNECTED PUMPS ASSOCIATED INTO ONE FUNCTIONALLY INDISSOCIABLE UNIT

The present invention relates to a total artificial heart comprising two disconnected pumps associated into one functionally indissociable unit.

French Patent Application No. 83 18368 filed on Nov. 18, 1983, which corresponds to U.S. Ser. No. 672,376, filed on Nov. 16, 1984, and U.S. Pat. No. 4,623,350, each describe a total artificial heart comprising two pumps, respectively representative of the right-hand part of the heart and of the left-hand part of the heart, as well as a device for controlling said pumps, this prosthesis being noteworthy in that, on the one hand, it comprises the indissociable functional unit constituted by:

a pericardial module adapted to be housed in the cavity of the natural heart to be replaced and enclosed in a tight envelope presenting four orifices for connection respectively to the right atrium, the pulmonary artery, the left atrium and the aorta, said orifices for connection to the right atrium and to the pulmonary artery being provided with valves to serve respectively as inlet orifice and outlet orifice for a first pump housed in said pericardial module and intended to perform the function of the right-hand part of the natural heart to be replaced;

an extra-pericardial module adapted to be housed in a physiologically neutral space in the receiver patient and to perform the function of the left-hand part of the natural heart to be replaced, this extra-pericardial module comprising a tight envelope in which is enclosed a second pump provided with an inlet orifice and an outlet orifice, each provided with a valve;

a functional link between said pericardial and extra-pericardial modules comprising:

a first conduit passing through the envelope of said pericardial module and joining the orifice of the latter corresponding to the left atrium and the inlet orifice of said second pump incorporated in said extra-pericardial module;

a second conduit passing through the envelope of said pericardial module and joining the orifice of the latter corresponding to the aorta and the outlet orifice of said second pump incorporated in said extra-pericardial module;

a third conduit establishing a gaseous communication between the sides of said first and second pumps opposed to the blood passing therethrough;

and in that, on the other hand, said control device actuates said pumps in opposition.

Thus, thanks to the separate, although monoblock and indissociable, structure of the prosthesis according to the invention, only said pericardial module, i.e. the right-hand part of the heart, lies in the pericardial cavity. The necessary space is in that case available for housing therein an envelope enclosing a pump and its electro-mechanical actuation system, acting as right ventricle.

This envelope of said pericardial module presents at least approximately the form of the diseased natural heart to be replaced, and, on said envelope, the arrangement of the orifices for connection to the right atrium, the pulmonary artery, the left atrium and the aorta corresponds at least substantially to the natural arrangement of these atria and arteries. In fact, the space made free in the pericardial cavity by moving away the pump acting as left-hand part of the heart, makes it possible to arrange said pericardial module so that the join to the veins and arteries is the optimum possible.

In such an artificial heart, it is the thoracic part of the aorta which is connected to the pericardial module, with the result that an artificial link (the second conduit) is provided between the two modules to extend the aorta.

In certain cases, rather than provide such an artificial link, it may be preferable to use the aorta itself.

It is an object of the present invention to allow such a use.

To this end, according to the invention, the total artificial heart comprising two pumps, respectively representative of the right-hand part of the heart and of the left-hand part of the heart, as well as a device for controlling said pumps, is noteworthy in that, on the one hand, it comprises the indissociable functional unit constituted by:

a pericardial module adapted to be housed in the cavity of the natural heart to be replaced and enclosed in a tight envelope presenting three orifices for connection respectively to the right atrium, the pulmonary artery and the left atrium, said orifices for connection to the right atrium and to the pulmonary artery being provided with valves to serve respectively as inlet orifice and outlet orifice for a first pump housed in said envelope and intended to perform the function of the right-hand part of the natural heart to be replaced;

an extra-pericardial module adapted to be housed in a space in the abdominal cavity of the receiver patient and to perform the function of the left-hand part of the natural heart to be replaced, this extrapericardial module comprising a second pump enclosed in a tight envelope, provided with an inlet orifice and an outlet orifice, each provided with a valve, said outlet orifice being connected to the abdominal part of the aorta;

a functional link between said modules comprising:

a first tube passing through said envelope of said pericardial module and joining the orifice of the latter corresponding to the left atrium and the inlet orifice of the second pump incorporated in said extra-pericardial module;

a second tube establishing a gaseous communication between the sides of said first and second pumps opposed to the blood passing therethrough;

and in that, on the other hand, said control device actuates said pumps in opposition.

In this way, according to the invention, with respect to the prosthesis mentioned above, the orifice of the pericardial module intended to be connected to the aorta, as well as the second conduit, may be eliminated, the first and second tubes of the prosthesis according to the present invention corresponding respectively to the first conduit and to the third conduit of the prior art prosthesis.

The prosthesis according to the present invention may therefore present all the advantages of this prior art prosthesis, namely:

(A) It in no way disturbs the venous blood return via the venae cavae and the pulmonary veins and it is then possible to adjust the beat frequency of the prosthesis as a function of the return pressure of the blood in the right-hand part of the heart, which is particularly advantageous. Consequently, a sensor may be disposed in said pericardial module to detect the pressure of the venous blood entering in said first pump and to regulate operation of the prosthesis as a function of the pressure measured.

(B) The moving away of the left-hand part of the heart from the pericardial cavity makes it possible to provide sufficient space to house, in said pericardial module, an electro-mechanical system for actuating said first pump, as well as the mechanisms for controlling electro-controlled valves.

(C) Said first pump may be of the diaphragm type and said electro-mechanical system may then be of the type with pusher-plate in direct contact with said diaphragm. It is therefore possible to optimalize the biological qualities of the prosthesis according to the invention, by shaping said plate so that it causes the minimum of mechanical stresses leading to the formation of micro-cracks in the diaphragm, these micro-cracks being, in known manner, the origin of the degradation of the quality of the driving diaphragm of the prosthesis. Moreover, the sensor mentioned above and intended to regulate the operation of the prosthesis may then be mounted on the diaphragm of said first pump.

(D) Since the extra-pericardial module is housed in an abdominal volume which is easily accessible by a minor surgical operation, said extra-pericardial module which is the power module and therefore the one most subject to wear, may, in the event of breakdown, easily be replaced by a new, irreproachably operating module.

To facilitate such an exchange, it is advantageous if the envelope of said extra-pericardial module presents connecting orifices respectively connected to the inlet orifice, the outlet orifice and to the side of said second pump opposed to the blood and adapted to be easily and respectively connected and disconnected from said first tube, the connection to the abdominal aorta and said second tube.

(E) Since the volume of the abdominal space may be relatively large (up to one liter), there is no problem of space requirement, and said extra-pericardial module may also incorporate a high-yield electro-mechanical system for direct actuation of said second pump. The latter may also be of the diaphragm type, with the result that the electromechanical system associated therewith is then of the type with pusher plate in direct contact with this diaphram.

(F) For the above reason, each of the two valves incorporated in said extra-pericardial module may be of the type with controlled opening and closure, like those provided for said pericardial module. It is then advantageous if the device for controlling the prosthesis comprises a microprocessor controlling the electro-mechanical systems incorporated in said modules, as well as the four valves thereof. This microprocessor then receives the information from the sensor disposed in said pericardial module and enabling the cardiac rhythm to be adjusted to the patient's needs.

Said link preferably joins the lower part of the envelope of said pericardial module to the upper part of the envelope of said extra-pericardial module.

According to an important feature of the present invention, said second tube of said link between said pericardial and extra-pericardial modules is longitudinally supple but radially rigid and it encloses said first tube.

This first tube is thus protected mechanically by the second. This is particularly advantageous as said first tube must be very supple, therefore very thin, and must not undergo any provoked pressure drop. Said first tube, associated with the interior space of said second tube, then acts as complementary left atrium. It will be noted that, thanks to said second tube, said link between the modules serves as compliance chamber for the whole of the prosthesis.

An electric cable may be passed in this second tube, joining said pericardial and extra-pericardial modules. In this way, control of the electro-mechanical system and of the valves of said pericardial module may pass via said extra-pericardial module and said electric cable contained in the link.

The invention will be more readily understood on reading the following description with reference to the accompanying drawings, in which identical references designate like elements. Moreover, in these Figures, elements identical to those shown in the Figures of French Patent Application No. 83 18368 bear identical references. (See also U.S. Pat. No. 4,623,350)

FIG. 1 schematically shows a natural heart linked with its principal veins and arteries, in front view.

FIG. 2 is an operational diagram of the heart of FIG. 1.

FIG. 3 schematically illustrates the artificial heart described in the Patent Application mentioned hereinabove.

FIG. 4 shows the diagram of the artificial heart according to the present invention.

Figure 5:
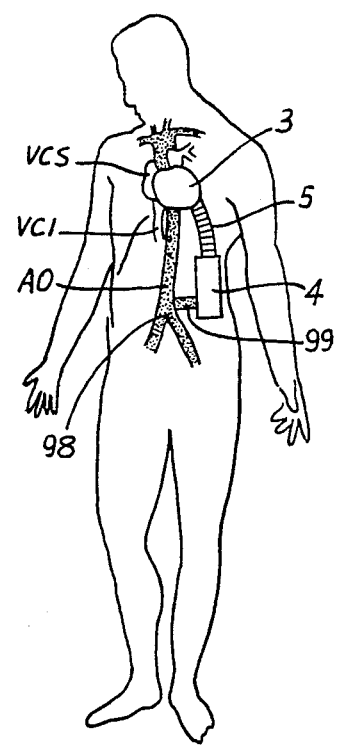

FIG. 5 schematically illustrates the prosthesis according to the invention in position in a patient.

Figure 6:
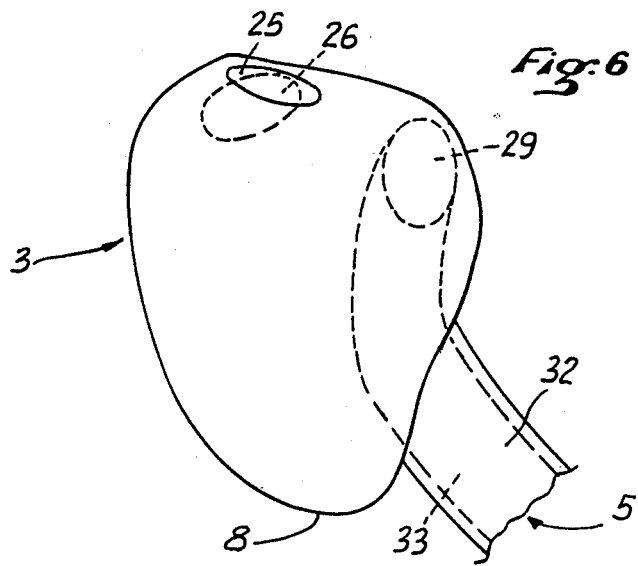

FIG. 6 schematically shows, from the outside, an embodiment of the pericardial module and the start of said link between the modules.

Referring now to the drawings, and as schematically illustrated in FIGS. 1 and 2, a natural human heart 1 is housed in the pericardial cavity 2 (simply illustrated by a broken line 2) and is in fact composed of two hearts, which are distinct, but fast with each other, namely the right heart CD comprising the right atrium OD and the right ventricle VD and the left heart CG comprising the left atrium OG and the left ventricle VG. The atrium OD of the right heart CD receives the venous blood via the superior vena cava VCS and via the inferior vena cava VCI, whilst the ventricle VD of said right heart CD causes the blood thus received to pass towards the lungs via the pulmonary artery AP.

Similarly, the atrium OG of the left heart CG receives the blood coming from the lungs via the left and right pulmonary veins VPG and VPD respectively and the ventricle VG of the left heart CG expels the blood received via the aorta AO.

The basic concept of the prosthesis incorporating disconnected pumps of the type to which the present invention relates, is based on the physiological observation that, although constituted by two pumps CD and CG forming a single muscular unit, the heart 1 is in fact composed of two functionally independent assemblies. In fact, from the functional standpoint, the right heart CD may be considered as a simple heart of passage which pushes a column of blood of which the flow speed is variable, but never zero, except when the frequencies of the beats of heart 1 are very low. When the blood flowrate of the vascular system increases further to an increase in frequency of these beats, the participation of the right heart CD in the movement of the blood in the pulmonary circuit decreases due to the increase of the speed, and therefore of the kinetic energy, of the blood arriving at the right heart CD. On the other hand, the left heart CG, by its powerful ventricle, constitutes the heart proper, i.e. the propulsive pump which ensures the perfusion of blood in all the organs and tissues of the organism.

Moreover, this basic concept is based on the fact known to the man skilled in the art that the contraction of the ventricle of the right heart CD and that of the ventricle of the left heart CG may be, not simultaneous, but in phase opposition.

As illustrated very schematically in FIG. 3, the total artificial heart described in the Patent Application mentioned above is constituted by a functionally indissociable unit constituted by two pumping modules 3 and 4 disconnected, but joined to each other by a tubular functional link 5.

The pumping module 3, intended to replace the right heart CD of the natural heart 1, is housed in the pericardial cavity 2. It comprises a tight envelope 8 on which are mounted four connecting means 25, 26, 29 and 30 of any known type, respectively intended to connect it to the right atrium OD (reservoir of the venae cavae VCI and VCS), the pulmonary artery AP, the left atrium OG (reservoir of the pulmonary veins VPG and VPD) and the aorta AO, after cut of the latter and excision of the natural atria from the pericardial cavity 2.

Orifices 25 and 26 for connection to the right atrium OD and to the pulmonary artery AP are provided with valves 27, 28 to serve respectively as inlet orifice and outlet orifice for a pump 13, 14 housed in the envelope 8 and intended to perform the function of the right-hand part of the natural heart to be replaced.

The pumping module 4, intended to perform the role of the left heart CG of the natural heart 1, is housed outside the pericardial cavity 2, in a physiologically neutral space, for example the thorax or the abdomen. It comprises a tight envelope 40 enclosing a pump 50, 52 provided with an inlet orifice 53 and an outlet orifice 56, each equipped with a valve 54 or 57.

The functional link 5, which may, without inconvenience, pass through the diaphragm of the patient receiving the prosthesis, comprises:

a first conduit 33 ensuring connection between orifice 29 of the pericardial module 3 corresponding to the left atrium OG and the inlet orifice 53 of the pump 50, 52 incorporated in the extra-pericardial module 4;

a second conduit 34 ensuring connection between orifice 30 of the pericardial module 3 corresponding to the aorta AO and the outlet orifice 56 of said pump 50, 52 incorporated in said extra-pericardial module 4;

a third conduit 32 establishing a gaseous communication between the sides of pumps 13, 14 and 50, 52 opposed to the blood passing therethrough.

In addition, a control device 89, 90, 92, 93 actuates pumps 13, 14 and 50, 52 in opposition and controls valves 27, 28, 54 and 57.

FIG. 4 shows, in a diagram comparable to that of FIG. 3, the prosthesis according to the present invention. This prosthesis is similar in all respects to that of FIG. 3, except in that envelope 8 of the pericardial module 3 does not comprise an orifice 30 and link 5 does not comprise a conduit 34.

In that case (cf. also FIG. 5), orifice 56 of the extra-pericardial module 4 is directly connected to the abdominal part 98 of the aorta AO via a connection 99.

Although this has not been shown in the drawings, orifices 25, 26, 29 and 56 are, of course, provided with connection devices.

As shown in FIG. 6, tube 33 is enclosed in tube 32 and, on the pericardial module 3 side, these two tubes may be fast therewith. On the other hand, on the abdominal module 4 side, a rapid connection (not shown) may be provided.

Tube 32 presents a sufficient longitudinal suppleness to enable it optimally to fit by flexion, without crushing, the physiological passage which may exist between the pericardial cavity 2 in which the pumping module 3 is disposed and the abdominal cavity in which the pumping module 4 is placed. On the other hand, tube 32 presents considerable radial rigidity in order to avoid any formation of folds and any outside compression. To that end, this tube 32 may for example comprise in its wall a spirally wound wire or the like. The diameter of the tubular envelope 32 may be of the order of 5 cm.

Inside said tube 32, as mentioned hereinabove, passes the supple tube 33 extending into a common pulmonary vein the left atrium into which open out the left and right pulmonary veins and an electrical connection (not shown) joining the pumping module 3 to the pumping module 4 and to an electric generator (not shown). The electrical connection allows supply and servo-control of the motor for actuating pump 13, 14 and of the electro-controlled valves disposed in orifices 25 and 26.

Supple tube 33 must present a section greater than 8 cm$^2$ in order to avoid pressure drops.

Inside the tubular envelope 32, tube 33 and said electrical connection leave a free space placing the dead spaces of the two pumping modules 3 and 4 into gaseous communication.

The following comments may be made concerning the structure of link 5:

1—In order to fit the left atrium and the pulmonary veins, tube 33 must be very supple and present an identical consistency, similar to a windbag. Tube 33 is therefore very fragile. However, this is not a drawback as, in link 5, tube 33 is well protected by the more rigid tube 32.

2—The free interior space in tube 32 places the dead spaces of the pumping modules 3 and 4 into communication. The latter functioning in opposition, said free interior space therefore allows the gaseous volume driven out by the pump of one of said modules, to move towards the other of said modules.

It therefore serves as volume compensation chamber necessitated by the operation of diaphragm pumps incorporating pusher-plate. Moreover, it makes it possible to balance the variations in atmospheric pressure since the blood contained in the common pulmonary vein 33 is in equilibrium with atmospheric pressure. This interior space therefore elegantly solves the delicate problem of the "compliance" chamber, mentioned by numerous authors.

3—The pump of the extra-pericardial power module 4 risks provoking hydraulic jolts in tube 33 extending the left atrium. However, this is not a drawback. In fact, in the event of hydraulic jolts, tube 33, of which the consistency is very supple, expands radially, this being possible due to the existence of the free pneumatic space within tube 32. In this way, tube 33 in association with this free space performs the role of a blood reservoir, in the manner of an atrium: it may therefore be considered as a complementary left atrium.

4—In order to complete the buffer function of said free space, the envelope or wall (this may be a part of envelope 8) surrounding tube 33, may possibly be arranged, within the pericardial module 3, to be supple instead of being rigid.

FIG. 6 shows that envelope 8 of the pericardial module 3 may present, at least approximately, the shape, volume and mass of the natural heart 1 to be replaced and that, on said envelope, the arrangement of orifices 25, 26 and 29 for connection to the right atrium, the pulmonary artery and the left atrium corresponds at least substantially to the natural arrangement of these atria and artery.

What is claimed is:

1. A total cardiac prosthesis comprising two pumps, respectively representing the right heart and the left heart, as well as a control device of said pumps (89, 90, 92, 93), actuating said pumps in opposition, said prosthesis also comprising an undissociable functional unit formed of:
   a pericardial unit (3) destined to be housed in the cavity (2) of the natural heart to be replaced (1) and enclosed in a tight envelope (8) provided with three coupling orifices (25, 26, 29), respectively adapted to be connected to the right auricle RA, to the pulmonary artery PA and to the left auricle LA, said orifices (25 and 26) for coupling for the right auricle and the pulmonary artery PA being provided with valves used respectively as inlet orifice and outlet orifice of a first pump (13, 14) housed in said envelope (8) and destined to assume the right heart function of the natural heart to be replaced;
   an extra-pericardial unit (4) destined to be housed in the abdominal cavity of the receiving sick person and to assume the function of the left heart of the natural heart to be replaced (1), said extra-pericardial unit comprising a second pump (50, 52) enclosed in a tight envleope (40) provided with an inlet orifice (53) and an outlet orifice (56), each provided with a valve said outlet orifice (56) being coupled to the abdominal part of the aorta;
   a functional connection line (5) between said units, comprising:
   a first duct (33) passing through said envelope (8) of said pericardial unit (3) and connecting the orifice (29) of the latter corresponding to the left auricle LA with the inlet orifice (53) of the section pump (50, 52) incorporated into said extra-pericardial unit (4),
   a duct (32) establishing communication for the gases between the sides of said first and second pumps opposite top the blood flow therethrough.

2. The total artificial heart of claim 1, wherein said pericardial unit encloses an electromechanical system for actuating said first pump.

3. The total artificial heart of claim 1, wherein said envelope of said pericardial unit presents at least approximately the form, volume and mass of the natural heart to be replaced, and, on said envelope, the arrangement of the orifices for connection to the right atrium, the pulmonary artery and the left atrium corresponds at least substantially to the natural arrangement of these artria and artery.

4. The total artificial heart of claim 1 wherein, in said pericardial unit, the valves provided in the orifices for connection to the right atrium and pulmonary artery are of the electro-controlled type.

5. The total artificial heart of claim 1 wherein said first pump is of the diaphragm and pusher-plate type.

6. The total artificial heart of claim 1, wherein said link connects the lower part of said envelope of said pericardial unit to the upper part of said envelope of said extra-pericardial module.

7. The total articifial heart of claim 2, wherein said second tube of said link between the units is longitudinally supple but radially rigid and encloses said first tube.

8. The total artificial heart of claim 1, wherein said second pump is of the diaphragm and pusher-plate type.

9. The total artificial heart of claim 1, wherein each of the two valves incorporated in said extra-pericardial unit is of the electro-controlled type.

* * * * *